(12) United States Patent
Stewart

(10) Patent No.: US 9,198,906 B2
(45) Date of Patent: Dec. 1, 2015

(54) KETOCONAZOLE ENANTIOMER IN HUMANS

(75) Inventor: Timothy Andrew Stewart, San Francisco, CA (US)

(73) Assignee: Cortendo AB (publ), Partille (SE)

(*) Notice: Subject to any disclaimer, the term of this patent is extended or adjusted under 35 U.S.C. 154(b) by 1184 days.

(21) Appl. No.: 12/443,531

(22) PCT Filed: Oct. 2, 2007

(86) PCT No.: PCT/US2007/080186
§ 371 (c)(1),
(2), (4) Date: Nov. 9, 2009

(87) PCT Pub. No.: WO2008/042898
PCT Pub. Date: Apr. 10, 2008

(65) Prior Publication Data
US 2010/0093755 A1    Apr. 15, 2010

Related U.S. Application Data

(60) Provisional application No. 60/848,963, filed on Oct. 2, 2006.

(51) Int. Cl.
| A61K 31/496 | (2006.01) |
| A61K 31/00  | (2006.01) |
| A61K 31/40  | (2006.01) |
| A61K 45/06  | (2006.01) |

(52) U.S. Cl.
CPC .............. *A61K 31/496* (2013.01); *A61K 31/00* (2013.01); *A61K 31/40* (2013.01); *A61K 45/06* (2013.01)

(58) Field of Classification Search
CPC .................................................. A61K 31/496
See application file for complete search history.

(56) References Cited

U.S. PATENT DOCUMENTS

| 4,144,346 | A | 3/1979 | Heeres et al. |
| 4,503,055 | A | 3/1985 | Heeres et al. |
| 5,584,790 | A | 12/1996 | Bell et al. |
| 5,849,740 | A | 12/1998 | Märin |
| 6,040,307 | A | 3/2000 | Gray et al. |
| 6,133,280 | A | 10/2000 | Brodie et al. |
| 6,166,017 | A | 12/2000 | Marin |
| 6,177,247 | B1 | 1/2001 | Mathies et al. |
| 6,642,236 | B1 | 11/2003 | Marin |
| 7,872,008 | B2 | 1/2011 | Marin |
| 7,960,410 | B2 | 6/2011 | Marin |
| 2002/0055512 | A1 | 5/2002 | Marin et al. |
| 2003/0190357 | A1 | 10/2003 | Marin et al. |
| 2004/0029891 | A1 | 2/2004 | Ghazzi et al. |
| 2004/0180868 | A1 | 9/2004 | Mullally |
| 2005/0013834 | A1 | 1/2005 | Ljusberg et al. |
| 2006/0002999 | A1 | 1/2006 | Yang et al. |
| 2007/0116839 | A1* | 5/2007 | Prakash ............... A23L 1/22075 426/548 |
| 2009/0233843 | A1 | 9/2009 | Marin |
| 2010/0280046 | A1 | 11/2010 | Stewart |

FOREIGN PATENT DOCUMENTS

| CA | 2397065 A1 | 7/2001 |
| CA | 2594433 A1 | 7/2006 |
| EP | 1853266 B1 | 10/2011 |
| JP | 2001-513082 A | 8/2001 |
| JP | 2003-503448 A | 1/2003 |
| JP | 2003-520788 A | 7/2003 |
| WO | WO 89/07442 A1 | 8/1989 |
| WO | WO 94/14446 A1 | 7/1994 |
| WO | WO 94/14462 A2 | 7/1994 |
| WO | WO 94/27990 A1 | 12/1994 |
| WO | WO 96/04912 A1 | 2/1996 |
| WO | WO 97/21435 A1 | 6/1997 |
| WO | WO 97/28149 A1 | 8/1997 |
| WO | WO 98/04528 A2 | 2/1998 |
| WO | WO 98/36770 A1 | 8/1998 |
| WO | WO 99/01423 A1 | 1/1999 |
| WO | WO 00/39088 A1 | 7/2000 |
| WO | WO 00/42026 A1 | 7/2000 |
| WO | WO 00/58360 A2 | 10/2000 |
| WO | WO 00/59887 A1 | 10/2000 |
| WO | WO 00/69810 A1 | 11/2000 |
| WO | WO 01/23420 A2 | 4/2001 |
| WO | WO 01/52833 A1 | 7/2001 |
| WO | WO 02/00681 A1 | 1/2002 |
| WO | WO 03/011258 A1 | 2/2003 |
| WO | 03026573 A2 | 4/2003 |
| WO | WO 03/27095 A1 | 4/2003 |
| WO | WO 03/27225 A2 | 4/2003 |
| WO | WO 2004/052390 A2 | 6/2004 |
| WO | WO 2005/113516 A1 | 12/2005 |
| WO | 2006072881 A1 | 7/2006 |

(Continued)

OTHER PUBLICATIONS

Han et al 'Prospective Study of C-Reactive Protein in Relationship to the Development of Diabetes and Metabolic Syndrome in the Mexico City Diabetes Study' Diabetes Care, vol. 25, p. 2016-2021, 2002.*
Willerson JT1, Ridker PM. Inflammation as a cardiovascular risk factor. Circulation. Jun. 1, 2004;109(21 Suppl 1):II2-10.*
Bennett JE, "Antimicorbial Agents (Continued) Antifungal Agents," Goodman & Gilman's The Pharmacological Basis of Therapeutics 10th ed., 2001, Hardman JG, Limbird LE, and Gilman AG, Eds, McGraw-Hill, New York 2001, 1295-1312 (pp. 1295 and 1301 provided).*
Liebel F, Lyte P, Garay M, Babad J, Southall MD. Anti-inflammatory and anti-itch activity of sertaconazole nitrate. Arch Dermatol Res. Sep. 2006;298(4):191-9. Epub Jul. 26, 2006.*
Brass, et al.; "Disposition of Ketoconazole, an Oral Antifungal, in Humans"; Antimicrobial Agents and Chemotherapy; 21; pp. 151-158; (1982).

(Continued)

*Primary Examiner* — Paul Zarek
(74) *Attorney, Agent, or Firm* — Maryellen Feehery Hank; Reed Smith LLP

(57) ABSTRACT

Treatment of patients with the 2S,4R ketoconazole enantiomer or its pharmaceutically acceptable salts, hydrates, and solvates is useful for reducing systemic inflammation and cholesterol levels and improving glycemic control.

18 Claims, 7 Drawing Sheets

(56) References Cited

FOREIGN PATENT DOCUMENTS

| WO | WO 2006/072881 A1 | 7/2006 |
|---|---|---|
| WO | WO 2007/081980 A2 | 7/2007 |
| WO | WO 2008/042898 A2 | 4/2008 |
| WO | 2012052540 A1 | 4/2012 |

OTHER PUBLICATIONS

Dutreix, et al.; "Pharmacokinetic Interaction Between Ketoconazole and Imatinib Mesylate (Glivec) in Healthy Subjects"; Cancer Chemother Pharmacol; 54; pp. 290-294; (2004).
Glynn, et al.; "Effects of Ketoconazole on Methylprednisolone Pharmacokinetics and Cortisol Secretion"; Clin Pharmacol Ther; 39; pp. 654-659; (1986).
Gylling, et al.; "Effects of Ketoconazole on Cholesterol Precursors and Low Density Lipoprotein Kinetics in Hypercholesterolemia"; Journal of Lipid Research; 34; pp. 59-67; (1993).
Janssen, et al.; "Hepatic Reactions During Ketoconazole Treatment"; The American Journal of Medicine; pp. 80-85; (Jan. 24, 1983).
Lutgens, et al.; "HMG-coA Reductase Inhibitors: Lipid-Lowering and Beyond"; Drug Discovery Today; 1; pp. 189-194; (2004).
Ma et al.; "Hepatotoxicity and Toxicokinetics of Ketoconazole in Rabbits"; Acta Pharmacol Sin; 24; pp. 778-782; (2003).
Morganroth, et al.; "Lack of Effect of Azelastine and Ketoconazole Coadministration on Electrocardiographic Parameters in Healthy Volunteers"; J. Clin Pharmacol; 37; pp. 1065-1072; (1997).
Rotstein, et al.; "Stereoisomers of Ketoconazole: Preparation and Biological Activity" J. Med. Chem.; 35; pp. 2818-2825; (1992).
Smith, et al.; Ketoconazole: An Orally Effective Antifungal Agent; Pharmacotherapy; 4; pp. 199-204; (1984).
Sohn, Catherine Angell; "Evaluation of Ketoconazole"; Clinical Pharmacy; 1; pp. 217-224; (1982).
Sonino, et al.; Ketoconazole Treatment in Cushing's Syndrome: Experience in 34 Patients; Clinical Endocrinology; 35; pp. 347-352; (1991).
International Search Report; International Application No. PCT/US07/80186; International Filing Date Oct. 2, 2007; Date of Mailing: Jul. 28, 2008; 2 pages.
Dimmeler, et al.; "HMG-CoA Reductase Inhibitors (statins) Increase endothelial Progenitor Cells Via the PI3-kinase/Akt Pathway"; Journal of Clinical Investigateion; 108; pp. 391-397; (2001).
Kang, et al.; "Relationship of Serum High Sensitivity C-reactive Protein to Meteabolic Syndrome and Microvascular Complications in Type 2 Diabetes"; Diabetes Research and Clinical Practice; 69; pp. 151-159; (2005).
Schwartz, et al.; "Safety Profile and Metabolic Effects of 14 Days of Treatment With DIO-902: Results of a Phase IIa Multicenter, Randomized, Double-Blind, Placebo-Controlled, Parallel-Group Trial in Patients wiith Type 2 Diabetes Mellitus"; Clinical Therapeutics; 30; No. 6; pp. 1081-1088; (2008).
Urbina, et al.; "Mevinolin (Lovastatin) Potentiates the Antiproliferative Effects of Ketoconazole and Terbinafine Against Trypanosoma (Schizotrypanum) Cruzi: In Vitro and In Vivo Studies"; Antimicrobial Agents and Chemotherapy; 37; No. 3; pp. 580-591; (1993).
Wells, Bernice; "Glucocorticoids in Type 2 Diabetes Mellitus and the Metabolic Syndrome"; Drug Development Research; 67; pp. 570-573; (2006).
EPO Supplementary Search Report; Application No. EP 07 868 351.3; Publication No. EP2076265; Date of Completion Aug. 5, 2010; 6 pages.
Arnon et al. "Cholesterol 7 alpha-Hydroxylase Knockout Mouse: A Model for Monohydroxy Bile Acid-Related Neonatal Cholestasis" Nov. 1998, *Gastroenterology* 115(5):1223-1228.
Diederich et al. "In the Search for Specific Inhibitors of Human 11 beta-hydroxysteroid-dehydrogenases (11β-HSDs): Chenodeoxycholic Acid Selectively inhibits 11β-HDS-I" 2000, *European Journal of Endocrinology* 142:200-207.
Erickson et al. "Hypercholesterolemia and Changes in Lipid and Bile Acid Metabolism in Male and Female cyp7A1-Deficient Mice" 2003, *Journal of Lipid Research* 44:1001-1009.

Farmer et al. "Comparative Tolerability of the HMG-CoA Reductase Inhibitors" 2000, *Drug Safety* 23(3):197-213.
Gaeta et al. "Ketoconazole Impairs Biliary Excretory Function in the Isolated Perfused Rat Liver" Jun. 1987, *Naunyn- Schmiedeberg's Arch. Pharmacol.* 335(6):697-700.
Gerber et al. "Stereoselective Pharmacokinetics (PK) of Oral Ketoconazole (K) in Healthy Subjects" Sep. 14-17, 2003, ACAAF Poster Abstract, 43rd ICAAC Abstracts; Chicago, Illinois; Reference A-1569 (one page).
Huang et al. "Pharmacokinetics and Dose Proportionality of Ketoconazole in Normal Volunteers" Aug. 1986, *Antimicrobial Agents and Chemotherapy* 30(2):206-210.
Ideyama et al. "YM116, 2-(1H-Imidazol-4-ylmethyl)-9H-carbazole, Decreases Adrenal Androgen Synthesis by Inhibiting C17-20 Lyase Activity in NCI-H295 Human Adrenocortical Carcinoma Cells" Feb. 1999, *Jpn. J. Pharmacol.* 79(2):213-220.
International Search Report dated Jul. 28, 2008 for PCT/US07/80186 (2 pages).
International Search Report dated May 12, 2006 for PCT/IB2006/000026.
Internet Publication "A Phase I/II a Study of the 2S,4R Enantiomer of Ketoconazole in Subjects With Type 2 Diabetes Mellitus" Feb. 2005, http://clinicaltrials.gov/ct2/show/NCT00302224.
Lake-Bakaar et al. "Hepatic Reactions Associated with Ketoconazole in the United Kingdom" Feb. 14, 1987, *British Medical Journal* 294:419-422.
Leighton et al. "Activation of the Silent Endogenous Cholesterol-7-Alpha-Hydroxylase Gene in Rat Hepatoma Cells: a New Complementation Group Having Resistance to 25-Hydroxycholesterol" Apr. 1991, *Molecular and Cellular Biology* 11(4):2049-2056.
Miettinen "Cholesterol Metabolism During Ketoconazole Treatment in Man" 1988, *Journal of Lipid Research* 29:43-51.
Norlin et al. "Oxysterol 7Alphalpha-Hydroxylase Activity by Cholesterol 7alpha-Hydroxylase (CYP7A)" 2000, *Journal of Biological Chemistry* 275:34046-34053.
Princen et al. "Ketoconazole Blocks Bile Acid Synthesis in Hepatocyte Monolayer Cultures and In Vivo in Rat by Inhibiting Cholesterol 7α-Hydroxylase" Oct. 1986, *J. Clin. Invest.* 78:1064-1071.
Pullinger et al. "Human Cholesterol 7α-hydroxylase (CYP7A1) Deficiency has a Hypercholesterolemic Phenotype" Jul. 1, 2002, *J. Clin. Invest.* 110(1):109-117.
Rodriguez et al. "Inhibition of Mitochondrial Function in Isolated Rat Liver Mitochondria by Azole Antifungals" 1996, *J. Biochem. Toxicology* 11(3):127-131.
Rodriguez et al. "Metabolism of Ketoconazole and Deacetylated Ketoconazole by Rat Hepatic Microsomes and Flavin-Containing Monooxygenases" 1997, *Drug Metabolism and Disposition* 25(6):772-777.
Rodriguez et al. "N-Deacetyl Ketoconazole-Induced Hepatotoxicity in a Primary Culture System of Rat Hepatocytes" Feb. 28, 1997, *Toxicology* 117(2-3):123-131.
Sapse "Cortisol, High Cortisol Diseases and Anti-Cortisol Therapy" 1997, *Psychoneuroendocrinology* 22(1):S3-S10.
SG Search Report and Written Opinion, International Application No. SG 200705135-2; International Filing Date Jan. 10, 2006; Date of Completion Feb. 5, 2009; 7 pages.
Stricker et al. "Ketoconazole-Associated Hepatic Injury. A clinicopathological study of 55 cases" 1986, *Journal of Hepatology* 3(3):399-406.
Van Cauteren et al. "Safety Aspects of Oral Antifungal Agents" Sep. 1990, *Br. J. Clin. Pract. Suppl.* 71:47-49.
Wachall et al. "Imidazole Substituted Biphenyls: A New Class of Highly Potent and In Vivo Active Inhibitors of P450 17 as Potential Therapeutics for Treatment of Prostate Cancer" Sep. 1999, *Bioorganic & Medicinal Chemistry* 7(9):1913-1924.
Whiting et al. "Bile Acid Synthesis and Secretion by Rabbit Hepatocytes in Primary Monolayer Culture: Comparison with Rat Hepatocytes" Feb. 6, 1989, *Biochimica et Biophysica Acta* 1001(2):176-184.

(56) References Cited

OTHER PUBLICATIONS

Pradhan et al. "Effects of Initiating Insulin and Metformin on Glycemic Control and Inflammatory Biomarkers Among Patients with Type 2 Diabetes—The Lancet Randomized Trial" Sep. 16, 2009 JAMA 302(11):1186-1194.

Abel et al. "Cortisol Metabolism in Vitro—III. Inhibition of Microsomal 6β-Hydroxylase and Cytosolic 4-ENE-Reductase" 1993, J. Steriod Biochem. Mol. Biol. 46(6):827-832.

Ariens "Stereochemistry, a Basis for Sophisticated Nonsense in Pharmacokinetics and Clinical Pharmacology" 1984, Eur. J. Clin. Pharmacol. 26:663-668.

Castro-Puyana et al. "Enantiomeric Separation of Ketoconazole and Terconazole Antifungals by Electrokinetic Chromatography: Rapid Quantitative Analysis of Ketoconazole in Pharmaceutical Formulations" Oct. 2005, *Electrophoresis* 26(20):3960-3968 (abstract only).

Chen et al. "Ketoconazole Induces G0/G1 Arrest in Human Colorectal and Hepatocellular Carcinoma Cell Lines" 2000, *Tox. Appl. Pharma.* 169:132-141.

International Search Report dated Sep. 24, 2007 for PCT/US07/00588.

Karadag et al. "The Value of C-reactive Protein as a Marker of Systemic Inflammation in Stable Chronic Obstructive Pulmonary Disease" 2008, *Eu. J. Int. Med.* 19:104-108.

Lechin et al. "Dramatic Improvement with Clonidine in Acute Pancreatitis with Elevated Catecholamine and Cortisol Plasma Levels: Report of Five Cases" 1992, *J. Med.* 23(5):339-351 (abstract only).

Medline Plus Extract "C-reacctive Protein", downloaded Aug. 2, 2012 from Medline Plus, Article 003356.

O'Rourke "Ketoconazole in the Treatment of Prostrate Cancer" Mar.-Apr. 2003, *Clin. J. Oncol. Nurs.* 7(2):235-236.

Wright et al. "Relative Potency of Testosterone and Dihydrotestosterone in Preventing Atrophy and Apoptosis in the Prostate of the Castrated Rat" 1996, *J. Clin. Invest.* 98:2558-2568.

Chapman et al. "Synthesis of diastereomeric ketoconazole analogs", Journal of Heterocyclic Chemistry, Nov. 1, 1990, pp. 2063-2068, vol. 27, No. 7, XP055125995.

* cited by examiner

The decrease in fructosamine is associated with increasing drug exposure

KETOCONAZOLE ENANTIOMER IN HUMANS

CROSS-REFERENCE TO RELATED APPLICATIONS

This application claims priority to U.S. provisional application No. 60/848,963, filed Oct. 2, 2006, the entire contents of which is incorporated herein by reference.

FIELD OF THE INVENTION

The invention relates to the use of an enantiomer of ketoconazole for treating diabetes and other conditions.

BACKGROUND OF THE INVENTION

Ketoconazole, 1-acetyl-4-[4-[[2-(2,4-dichlorophenyl)-2-[(1H-imidazol-1-yl)-methyl]-1,3-dioxolan-4-yl]methoxy]phenyl]piperazine, is a racemic mixture of the cis enantiomers (−)-(2S,4R) and (+)-(2R,4S). Racemic ketoconazole is an approved drug (NIZORAL®) for the treatment of fungal infections.

More recently, ketoconazole was found to decrease plasma cortisol and to be useful, alone and in combination with other agents, in the treatment of a variety of diseases and conditions, including type 2 diabetes, Metabolic Syndrome (also known as the Insulin Resistance Syndrome, Dysmetabolic Syndrome or Syndrome X), and other medical conditions that are associated with elevated cortisol levels. See U.S. Pat. Nos. 5,584,790; 6,166,017; and 6,642,236, each of which is incorporated herein by reference. Cortisol is a stress-related hormone secreted from the cortex of the adrenal glands. ACTH (adenocorticotropic hormone) increases cortisol secretion. ACTH is secreted by the pituitary gland, a process activated by secretion of corticotropin releasing hormone (CRH) from the hypothalamus.

Ketoconazole has also been reported to lower cholesterol levels in humans (Sonino et al. (1991). "Ketoconazole treatment in Cushing's syndrome: experience in 34 patients." *Clin Endocrinol (Oxf)*. 35(4): 347-52; Gylling et al. (1993) "Effects of ketoconazole on cholesterol precursors and low density lipoprotein kinetics in hypercholesterolemia." *J Lipid Res.* 34(1): 59-67) each of which is incorporated herein by reference). The 2S,4R enantiomer is more active against the cholesterol synthetic enzyme 14a-lanosterol demethylase than is the other (2R,4S) enantiomer (Rotstein et al. (1992) "Stereoisomers of ketoconazole: preparation and biological activity." *J Med Chem* 35(15): 2818-2). However, because cholesterol level in a human patient is controlled by the rate of metabolism and excretion as well as by the rate of synthesis it is not possible to predict from this whether the 2S,4R enantiomer of ketoconazole will be more effective at lowering cholesterol levels in a human patient.

The use of ketoconazole as a therapeutic is complicated by the effect of ketoconazole on the P450 enzymes responsible for drug metabolism. Several of these P450 enzymes are inhibited by ketoconazole (Rotstein et al., supra). This inhibition leads to an alteration in the clearance of ketoconazole itself (Brass et al., "Disposition of ketoconazole, an oral antifungal, in humans." *Antimicrob Agents Chemother* 1982; 21(1): 151-8, incorporated herein by reference) and several other important drugs such as Glivec (Dutreix et al., "Pharmacokinetic interaction between ketoconazole and imatinib mesylate (Glivec) in healthy subjects." *Cancer Chemother Pharmacol* 2004; 54(4): 290-4) and methylprednisolone (Glynn et al., "Effects of ketoconazole on methylprednisolone pharmacokinetics and cortisol secretion." *Clin Pharmacol Ther* 1986; 39(6): 654-9). As a result, the exposure of a patient to ketoconazole increases with repeated dosing, despite no increase in the amount of drug administered to the patient. This exposure and increase in exposure can be measured and demonstrated using the "Area under the Curve" (AUC) based on the concentration of the drug found in the plasma and the time period over which the measurements are made. The AUC for ketoconazole following the first exposure is significantly less than the AUC for ketoconazole after repeated exposures. This increase in drug exposure means that it is difficult to provide an accurate and consistent dose of the drug to a patient. Further, the increase in drug exposure increases the likelihood of adverse side effects associated with ketoconazole use. As noted above, ketoconazole inhibits several P450 enzymes responsible for drug metabolism and this inhibition can lead to increased plasma levels of drugs that are co-administered with ketoconazole. This increase in the plasma levels of co-administered drugs can prevent the optimal use of either of ketoconazole or the co-administered drug.

Rotstein et al. (Rotstein et al., supra) have examined the effects of the two ketoconazole cis enantiomers on the principal P450 enzymes responsible for drug metabolism and reported " . . . almost no selectivity was observed for the ketoconazole isomers" and, referring to drug metabolizing P450 enzymes: "[t]he IC50 values for the cis enantiomers were similar to those previously reported for racemic ketoconazole". This report indicated that both of the cis enantiomers could contribute significantly to the AUC problem observed with the ketoconazole racemate.

One of the adverse side effects of ketoconazole administration exacerbated by this AUC problem is liver reactions. Asymptomatic liver reactions can be measured by an increase in the level of liver specific enzymes found in the serum and an increase in these enzymes has been noted in ketoconazole treated patients (Sohn, "Evaluation of ketoconazole." *Clin Pharm* 1982; 1(3): 217-24, and Janssen and Symoens, "Hepatic reactions during ketoconazole treatment." *Am J Med* 1983; 74(1B): 80-5, each of which is incorporated herein by reference). In addition 1:12,000 patients will have more severe liver failure (Smith and Henry, "Ketoconazole: an orally effective antifungal agent. Mechanism of action, pharmacology, clinical efficacy and adverse effects." *Pharmacotherapy* 1984; 4(4): 199-204, incorporated herein by reference). As noted above, the amount of ketoconazole to which a patient is exposed increases with repeated dosing even though the amount of drug taken per day does not increase (the "AUC problem"). The AUC correlates with liver damage in rabbits (Ma et al., "Hepatotoxicity and toxicokinetics of ketoconazole in rabbits." *Acta Pharmacol Sin* 2003; 24(8): 778-782 incorporated herein by reference) and increased exposure to the drug is believed to increase the frequency of liver damage reported in ketoconazole treated patients.

Additionally, U.S. Pat. No. 6,040,307, incorporated herein by reference, reports that the 2S,4R enantiomer is efficacious in treating fungal infections. This same patent application also reports studies on isolated guinea pig hearts that show that the administration of racemic ketoconazole may be associated with an increased risk of cardiac arrhythmia, but provides no data in support of that assertion. However, as disclosed in that patent, arrhythmia had not been previously reported as a side effect of systemic racemic ketoconazole, although a particular subtype of arrhythmia, torsades de pointes, has been reported when racemic ketoconazole was administered concurrently with terfenadine. Furthermore several published reports (for example, Morganroth et al.

(1997). "Lack of effect of azelastine and ketoconazole coadministration on electrocardiographic parameters in healthy volunteers." *J Clin Pharmacol.* 37(11): 1065-72) have demonstrated that ketoconazole does not increase the QTc interval. This interval is used as a surrogate marker to determine whether drugs have the potential for inducing arrhythmia. U.S. Pat. No. 6,040,307 also makes reference to diminished hepatoxicity associated with the 2S,4R enantiomer but provides no data in support of that assertion. The method provided in U.S. Pat. No. 6,040,307 does not allow for the assessment of hepatoxicity as the method uses microsomes isolated from frozen tissue.

Thus, there remains a need for new therapies for treating diseases and conditions associated with elevated cortisol levels or activity or that may be treated by lowering cortisol level or activity that are as effective as ketoconazole but do not present, or present to a lesser degree, the issues of drug interactions and adverse side effects of ketoconazole. The present invention meets these and other needs.

SUMMARY OF THE INVENTION

In one aspect, the present invention relates to administration of a 3-hydroxy 3-methylglutaryl coenzyme A (HMG CoA) reductase inhibitor (statin) to a patient in need of such treatment, in combination with a therapeutically effective amount of 2S,4R ketoconazole enantiomer substantially or entirely free of the 2R,4S ketoconazole enantiomer (sometimes simply "2S,4R ketoconazole enantiomer"). As described infra, coadministration of the 2S,4R ketoconazole enantiomer changes the pharmocokinetic profile of the HMG CoA reductase inhibitor, reducing the Cmax for the HMG CoA reductase activity. This allows higher doses of the HMG CoA reductase inhibitor to be administered to a patient whilst avoiding side-effects that would be expected if the HMG CoA reductase inhibitor was administered as a monotherapy.

The HMG CoA reductase inhibitor coadministered with the 2S,4R ketoconazole enantiomer may be, for example and not limitation, atorvastatin, lovastatin, simvastatin, pravastatin, fluvastatin, rivastatin, itavastatin, or rosuvastatin. In one embodiment the HMG CoA reductase inhibitor is atorvastatin.

Usually, the 2S,4R ketoconazole enantiomer is administered at a daily dose of from 100 mg-600 mg. The patient treated using the 2S,4R ketoconazole enantiomer/HMG CoA reductase inhibitor cotherapy may be, for example, a patient with diabetes, a patient with metabolic syndrome, or a patient not diagnosed as diabetic.

In another aspect the invention relates to administration of a therapeutically effective amount of 2S,4R ketoconazole enantiomer to a patient who will benefit from reduced levels of C-reactive protein (CRP). CRP is an acute phase protein and elevated CRP is an indicator of systemic inflammation. Thus, agents that reduce CRP levels are considered to reduce systemic inflammation. Thus, the invention provides methods for reduction of systemic inflammation in a patient in need of such reduction, by administration of the 2S,4R ketoconazole enantiomer to the patient. Patients with either of type 2 diabetes or metabolic syndrome generally also have elevated systemic inflammation that increases the risk in these patients of cardiovascular disease. Current therapies inadequately treat the systemic inflammation in these patients.

CRP levels can be measured in a variety of assays. Preferably, the high-sensitivity C-reactive protein assay is used. In one embodiment, a patient with plasma CRP levels greater than 2.0 mg/L is considered to have elevated CRP indicative of systemic inflammation. In one embodiment of the invention the patient is treated using the 2S,4R ketoconazole enantiomer to reduce CRP level (or maintain the patient's CRP level at a reduced level). In one embodiment, a patient with plasma CRP levels greater than 3.0 mg/L is considered to have elevated CRP indicative of systemic inflammation. In one embodiment, a patient with plasma CRP levels greater than 4.0 mg/L is considered to have elevated CRP indicative of systemic inflammation. In one embodiment, a patient with plasma CRP levels greater than 5.0 mg/L is considered to have elevated CRP indicative of systemic inflammation. In one embodiment, a patient with plasma CRP levels greater than 10.0 mg/L is considered to have elevated CRP indicative of systemic inflammation.

In one example, the method involves (i) identifying or diagnosing a patient as diabetic, (ii) identifying or diagnosing the patient as in need of reduction of his/her CRP level, and (iii) administering a therapeutically effective dose of the 2S,4R ketoconazole enantiomer (e.g., from 100-600 mg/day for at least 14 days).

In one example, the method involves (i) identifying or diagnosing a patient has having metabolic disease, (ii) identifying or diagnosing the patient as in need of reduction of CRP level, and (iii) administering a therapeutically effective dose of the 2S,4R ketoconazole enantiomer (e.g., from 100-600 mg/day for at least 14 days).

In one example, the method involves (i) identifying or diagnosing the patient as in need of reduction of CRP level, and (ii) administering a therapeutically effective dose of the 2S,4R ketoconazole enantiomer (e.g., from 100-600 mg/day for at least 14 days). The patient treated using the 2S,4R ketoconazole enantiomer therapy may be, for example, a patient with diabetes, a patient with metabolic syndrome, or a patient not diagnosed as diabetic.

Patients with either of type 2 diabetes or metabolic syndrome also have elevated total and LDL cholesterol and these elevated lipids increase the risk in these patients of cardiovascular disease. Patients with type 2 diabetes are characterized by hyperglycemia and insulin resistance and patients with metabolic syndrome are characterized by several of the following: insulin resistance, elevated fasting glucose, dyslipidemia, hypertension, and central obesity. In many patients with either of type 2 diabetes or metabolic syndrome the elevated total and LDL cholesterol are inadequately treated.

The present invention provides methods for treatment of patients with either of type 2 diabetes or metabolic syndrome by administering 2S,4R ketoconazole enantiomer substantially or entirely free of the 2R,4S ketoconazole enantiomer at a daily dose of from 100 mg-600 mg, where the course of treatment results in a reduction in cholesterol levels and a reduction in CRP level, as well as improved glycemic control.

DETAILED DESCRIPTION OF THE INVENTION

Figure 1:
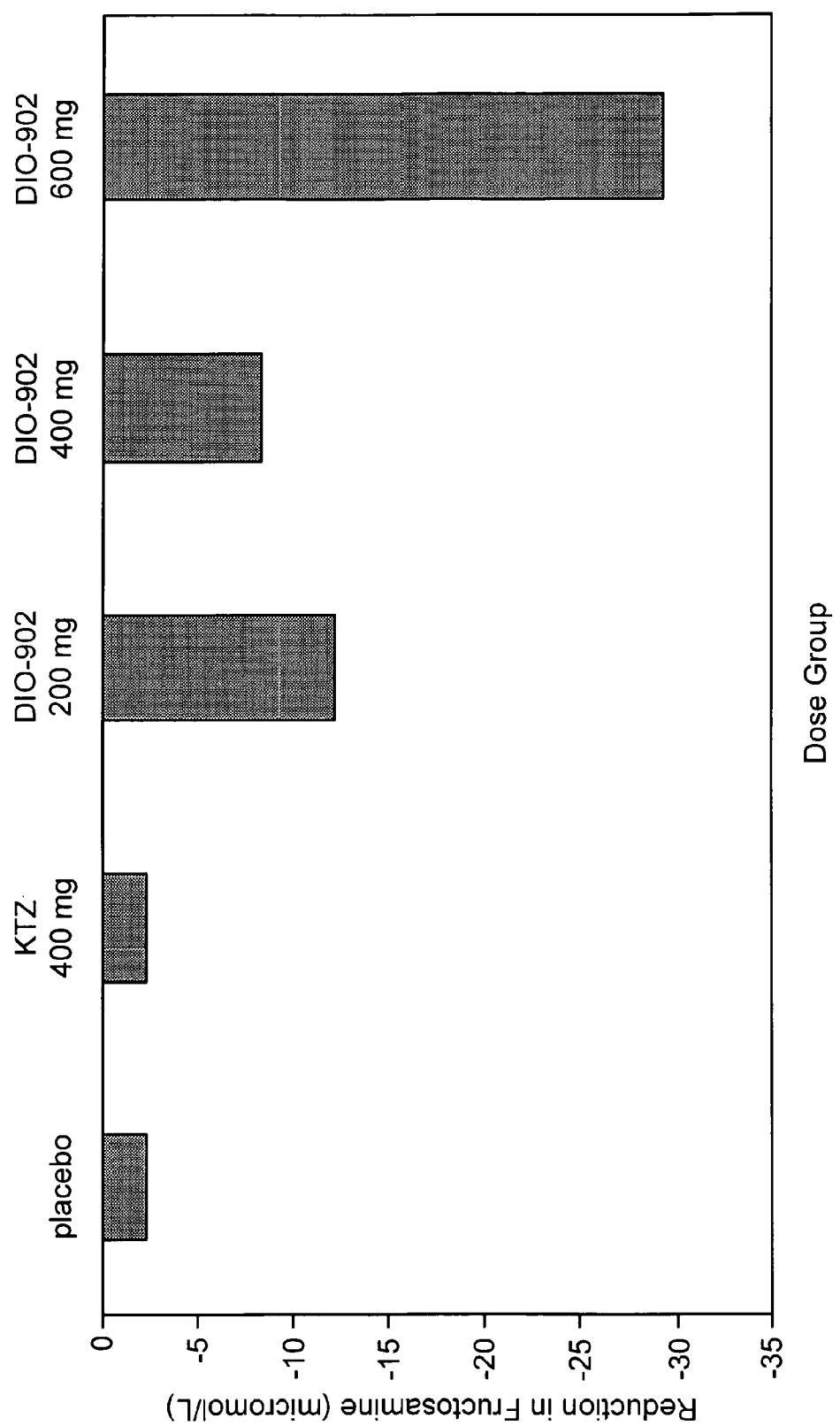
FIG. 1 shows the effect of a two-week administration of a ketoconazole enantiomer (DIO-902) on fructosamine levels.

The present invention provides for the therapeutic use of pharmaceutical compositions comprising the 2S,4R ketoconazole enantiomer substantially or entirely free of the 2R,4S enantiomer. "Substantially free" of the 2R,4S enantiomer, in one embodiment, means that the ketoconazole content of the pharmaceutical composition is less than 2% of the 2R,4S enantiomer and more than 98% of the 2S,4R enantiomer. In another embodiment, substantially free of the 2R,4S enantiomer means the ketoconazole content of the pharmaceutical composition is less than 10% of the 2R,4S enantiomer and more than 90% of the 2S,4R enantiomer. In another embodiment, substantially free of the 2R,4S enantiomer means that the ketoconazole content of the pharmaceutical composition is less than 20% of the 2R,4S enantiomer and more than 80% of the 2S,4R enantiomer.

The 2S,4R ketoconazole enantiomer and pharmaceutical compositions containing the 2S,4R ketoconazole enantiomer substantially or entirely free of the 2R,4S ketoconazole enantiomer, and pharmaceutically acceptable salts of the 2S,4R enantiomer of ketoconazole may be prepared as described in PCT Publication WO06072881 entitled "Methods And Compositions For Treating Diabetes, Metabolic Syndrome And Other Conditions," the entire contents of which are incorporated by reference. The 2S,4R ketoconazole enantiomer may be administered in a variety of unit dosage forms, frequencies, and routes of administration, as described in PCT Publication WO06072881.

"DIO-902," as used herein, refers to a pharmaceutical preparation of the 2S,4R ketoconazole enantiomer used in clinical trials. DIO-902 comprises 2S,4R ketoconazole purified from the racemic mixture and is largely (greater than 98%) free of the 2R,4S enantiomer. DIO-902 is an immediate release tablet to be taken orally and formulated as shown in Table 1, below.

TABLE 1

| Component | Percentage |
|---|---|
| 2S,4R ketoconazole | 50% |
| Silicified Microcrystalline Cellulose, NF (Prosolv HD 90) | 16.5 |
| Lactose Monohydrate, NF (316 Fast-Flo) | 22.4 |
| Corn Starch, NF (STA-Rx) | 10 |
| Colloidal Silicon Dioxide, NF (Cab-O-Sil M5P) | 0.5 |
| Magnesium Stearate, NF | 0.6 |

Importantly, it will be appreciated that the data, observations and conclusion reported in the Examples below are not intended to be limited to this particular DIO-902 formulation. The use of the 2S,4R ketoconazole enantiomer for lowering cholesterol and CRP levels, for improving glycemic control, and other uses as described herein is not limited to this particular formulation.

"Co-administration" and "co-therapy" refer to the administration of two (or more) drugs in the same course of therapy in order to achieve a type or level of benefit not resulting from administration of either drug individually.

"Administration" means administering a drug or combination of drugs for at least one day, more often for at least seven days, even more often for at least fourteen days, even more often for at least one month, often for at least 4 months (120 days), and sometimes for several years. "Administering" or "administration of" a drug to a subject (and grammatical equivalents of this phrase) may refer to direct administration, including self-administration, and indirect administration, including the act of prescribing a drug. For example, a physician who instructs a patient to self-administer a drug and/or provides a patient with a prescription for a drug may be administering the drug to the patient.

Administration of a therapeutically effective amount of the 2S,4R ketoconazole enantiomer substantially free of the 2R,4S enantiomer is effective in treating, controlling, and ameliorating the symptoms of diabetes, particularly type 2 diabetes. Administration of a therapeutically effective amount of the 2S,4R ketoconazole enantiomer substantially free of the 2R,4S enantiomer is also effective for treating a lipid disorder selected from the group consisting of dyslipidemia (e.g., hypercholesterolemia) in a human patient in need of such treatment.

As shown in the Examples, below, a two-week course of treatment with the 2S,4R ketoconazole enantiomer dramatically reduced cholesterol levels, improved glycemic control, and reduced levels of C-reactive protein in diabetic subjects. Most patients with type 2 diabetes have increased systemic inflammatory activity demonstrated by elevated plasma CRP (C reactive protein) in addition to elevated plasma glucose. This systemic inflammation is believed to contribute to the increased risk of cardiovascular disease. The systemic inflammation is poorly controlled by existing diabetes medications.

Based on this short-term result it is expected that administration of the 2S, 4R ketoconazole enantiomer for a longer period of time (e.g., four weeks, twelve weeks, twenty-six weeks, or longer) will have effects of greater magnitude than observed after two weeks treatment.

Usually the ketoconazole enantiomer is administered at a daily dose of from 100 to 600 mg, more usually at a dose of from 100 to 450 mg, and often at a dose of from 200 to 400 mg. Exemplary daily doses include 100, 125, 150, 200, 250, 300, 375, 400 or 450 mg. An example of the composition of a 150 mg strength, 300 mg weight tablet is described in Table 2.

TABLE 2

Composition of 150 mg strength (300 mg) weight tablet

| Component | Amount (mg) |
|---|---|
| 2S,4R ketoconazole | 150 |
| Silicified Microcrystalline Cellulose, NF (ProsolvHD 90) | 49.5 |
| Lactose Monohydrate, NF (316 Fast-Flo) | 67.2 |
| Corn Starch, NF (STA-Rx) | 30 |
| Colloidal Silicon Dioxide, NF (Cab-O-Sil M5P) | 1.5 |
| Magnesium Stearate, NF | 1.8 |

Administration of the ketoconazole enantiomer at an aforementioned dose beneficially results in a reduction in cholesterol levels compared to baseline. Administration of the ketoconazole enantiomer at an aforementioned dose beneficially results in improved glycemic control compared to baseline. Administration of the ketoconazole enantiomer at an aforementioned dose beneficially results in a reduction in CRP levels compared to baseline. As used herein, "baseline" means the level prior to commencement of therapy. In some embodiments, "baseline" is determined in a subject not receiving another therapy intended to reduce cholesterol and/or improve glycemic control (excluding therapy using insulin, glucagon or analogs of either) and/or reduce inflammation. Assessment of changes in markers at baseline and after the commencement of therapy can be based on measurements in a single patient or, more often, based on a statistically significant average or mean of several individuals or a large group of individuals. For example, a clinical endpoint (e.g., reduced cholesterol) may be based on an individual or on a statistically relevant group of individuals.

In one aspect, the invention provides a method for reducing cholesterol levels in a diabetic patient by administering a 2S,4R ketoconazole enantiomer substantially free of the 2R,4S ketoconazole enantiomer to said patient at a daily dose of from 100-600 mg, preferably 200-450 mg, where 14 days of treatment results in a reduction, compared to baseline, of LDL cholesterol by at least 15% and/or total cholesterol by at least 25%.

In one aspect, the invention provides a method for reducing cholesterol levels in a diabetic patient by administering a 2S,4R ketoconazole enantiomer substantially free of the 2R,4S ketoconazole enantiomer to said patient at a daily dose of from 100-600 mg, preferably 150 mg-500 mg, such as 150 mg-450 mg, or 200-450 mg, where 90 days of treatment results in a reduction, compared to baseline, of LDL cholesterol by at least 15%, at least 20% or at least 30% and/or reduction of total cholesterol by at least 15%, at least 20%, at least 30%, or at least 40%.

In one aspect, the invention provides a method for improving glycemic control in diabetic patient by administering a 2S,4R ketoconazole enantiomer substantially free of the 2R,4S ketoconazole enantiomer to said patient at a daily dose of from 100-600 mg, preferably 150 mg-500 mg, such as 150 mg-450 mg, or 200-450 mg, where 14 days of treatment results in a reduction, compared to baseline, of (a) HbA1c levels by at least 0.3% and/or (b) fructosamine levels by at least 10 umol/L and/or (c) fasting blood glucose levels by at least 15 mg/dL.

In one aspect, the invention provides a method for improving glycemic control in a diabetic patient by administering a 2S,4R ketoconazole enantiomer substantially free of the 2R,4S ketoconazole enantiomer to said patient at a daily dose of from 100-600 mg, such as 150 mg-500 mg, 150 mg-450 mg, or preferably 200-450 mg, where 90 days of treatment results in a reduction, compared to baseline, of (a) HbA1c levels by at least 0.4%, preferably at least 0.6%, and sometimes at least 0.8% and/or (b) fructosamine levels by at least 20 umol/L, preferably at least 30 umol/L, and sometimes at least 40 umol/L, and/or (c) fasting blood glucose levels by at least 20 mg/dL, preferably at least 25 mg/dL and sometimes at least 30 mg/dL.

In some embodiments the patient to whom ketoconazole enantiomer is administered is also treated with an antihyperglycemic agent, such as metformin.

In one aspect, the invention provides a method for reducing risk of developing vascular disease by administering the 2S,4R ketoconazole enantiomer substantially free of the 2R,4S ketoconazole enantiomer to said patient at a daily dose of from 100-600 mg, preferably 150 mg-500 mg, such as 150 mg-450 mg, 200 mg-450 mg, or 300 mg-450 mg, where 14 days of treatment results in a reduction CRP level of at least 15%, at least 25%, preferably at least 40%, and more preferably at least 45%. Administration of the 2S,4R ketoconazole enantiomer substantially free of the 2R,4S ketoconazole enantiomer, alone or in combination with other agents, is also indicated for, without limitation, prevention of cardiovascular disease, reducing risk of myocardial infarction, reducing the risk of stroke, and reducing the risk for revascularization procedures and angina.

In one aspect, the invention provides a method for reducing risk of developing vascular disease by administering a 2S,4R ketoconazole enantiomer substantially free of the 2R,4S ketoconazole enantiomer to said patient at a daily dose of from 100-600 mg, preferably 200-450 mg, where 90 days of treatment results in a reduction CRP level of at least 40%, and preferably at least 45%. Exemplary daily doses include 150 mg, 300 mg and 450 mg.

In one embodiment, administering a 2S,4R ketoconazole enantiomer substantially free of the 2R,4S ketoconazole enantiomer to said patient at a daily dose of from 100-600 mg, preferably 200-450 mg, results in improved glycemic control, and reduced cholesterol and reduced CRP.

In one embodiment, the aforementioned benefits result from a daily dose of from 100 to 450 mg of the 2S,4R ketoconazole enantiomer, such as from 200 to 400 mg (e.g., 150, 175, 200, 225, 250, 275, 300, 325, 350, 375, 400, 420 or 450 mg).

In one embodiment, after 14 or 90 days of therapy, the patient to whom drug is administered has alanine aminotransferase (ALT) aspartate aminotransferase (AST) and alkaline phosphatase (AP) levels in the normal range normal. In one embodiment, at least one liver function test level (AST/ALT/AP) of the patient was not in the normal range at baseline (prior to initiation of the therapy).

In another aspect, the invention provides a method for treatment of a diabetic patient by (a) administering a therapeutically effective amount of 2S,4R ketoconazole enantiomer substantially free of the 2R,4S ketoconazole enantiomer to the patient and (b) administering a therapeutically effective amount of a cholesterol-lowering HMG-CoA reductase inhibitor. In some embodiments the amount of HMG-CoA reductase inhibitor administered is greater than the amount indicated for the patient in the absence of administration of ketoconazole enantiomer (e.g., 20% greater, 50% greater, 100% greater (i.e., 2-fold greater) or more). In some embodiments the HMG-CoA reductase inhibitor is administered to a patient receiving ketoconazole enantiomer where administration of the HMG-CoA reductase inhibitor would be contraindicated in the patient in the absence of ketoconazole enantiomer. In some embodiments the HMG-CoA reductase inhibitor is lovastatin, simvastatin, pravastatin, fluvastatin, atorvastatin, rosuvastatin, itavastatin, ZD-4522, or rivastatin.

HMG-CoA reductase inhibitors are the primary treatment in the management of atherosclerotic vascular disease. The benefits of statin treatment are believed to result from their capacity to lower LDL-cholesterol (LDL-C). However, it has been suggested that lowering cholesterol alone cannot explain all of the beneficial effects of statin treatment. Recent findings suggest that statins invoke a generalized anti-inflammatory action (reviewed in Lutgens and Daemen, 2004, "HMG-coA reductase inhibitors: lipid-lowering and beyond" Drug Discovery Today: Therapeutic Strategies 1:189-194). The effects of 2S,4R ketoconazole enantiomer on cholesterol levels and systemic inflammation suggests an additive or synergistic effect when used in combination with a statin. Based on this observation, the dose of HMG-CoA reductase inhibitor administered to a patient may be reduced when a therapeutically effective amount of 2S,4R ketoconazole enantiomer is coadministered. Thus, in another aspect, the invention provides a method for reducing the amount of a HMG-CoA reductase inhibitor required to be administered to a patient for therapeutic efficacy, said method comprising administering a therapeutically effective amount of 2S,4R ketoconazole enantiomer substantially free of the 2R,4S ketoconazole enantiomer to the patient. In some embodiments the HMG-CoA reductase inhibitor is lovastatin, simvastatin, pravastatin, fluvastatin, atorvastatin, rosuvastatin, itavastatin, ZD-4522, or rivastatin.

In an other aspect, the invention provides a method for treatment of a diabetic patient by (a) administering a therapeutically effective amount of 2S,4R ketoconazole enantiomer substantially free of the 2R,4S ketoconazole enantiomer to the patient and (b) administering a therapeutically effective amount of a cholesterol-absorption inhibitor (e.g., ezitemibe).

In another aspect, the invention provides a method for the treatment of a non-diabetic patient with elevated cholesterol by administering a therapeutically effective amount of 2S,4R ketoconazole enantiomer substantially free of the 2R,4S enantiomer to the patient and (b) administering a therapeutically effective amount of a HMG-CoA reductase inhibitor. In some embodiments the amount of HMG-CoA reductase inhibitor administered is greater than the amount indicated for the patient in the absence of the administration of ketoconazole enantiomer (e.g., 20% greater, 50% greater, 100% greater (i.e., 2-fold greater) or more. In some embodiments the HMG-CoA reductase inhibitor is administered to a patient receiving ketoconazole enantiomer where administration of the HMG-CoA reductase inhibitor would be contraindicated in the patient in the absence of ketoconazole enantiomer. For illustration and not limitation, examples of HMG-CoA reductase inhibitors are lovastatin, simvastatin, pravastatin, fluvastatin, atorvastatin, rosuvastatin, itavastatin, ZD-4522 and rivastatin. Information concerning indications, contraindications and appropriate dosages (in the absence of ketoconazole enantiomer) is known and is readily available in the medical literature (e.g., see 2007 Physicians' Desk Reference, Thomson Corp., Toronto).

In another aspect, the invention provides a method for treatment of a diabetic patient presenting with abnormal level of at least one marker of liver function (e.g., ALT, AST or AP), where the patient is in need of treatment to reduce cholesterol and/or improve glycemic control, comprising administering a therapeutically effective amount of 2S,4R ketoconazole enantiomer substantially free of the 2R,4S ketoconazole enantiomer to the patient.

It has been reported that plasma pharmacokinetics of the two ketoconazole enantiomers are different. As demonstrated in the examples (see Example 4) it has now been discovered that the 2R,4S enantiomer is cleared from circulation by the liver much more rapidly than the 2S,4R enantiomer. The more rapid clearance of the 2R,4S enantiomer will result in a higher liver Cmax for this enantiomer as compared to the 2S,4R enantiomer. As a result, administration of the 2S,4R enantiomer substantially free of the 2R,4S enantiomer will result in a lower Cmax of ketoconazole in hepatocytes compared to administration of the racemate. That is, when ketoconazole is administered as the racemate the Cmax of the drug (sum of both enantiomers) in hepatocytes will be greater than the Cmax of the drug (single enantiomer) when administered as the 2S,4R enantiomer. Thus, surprisingly, administration of the 2S,4R enantiomer will produce a lower Cmax in hepatocytes and reduced likelihood of any liver toxicity (at any dose).

Examples

Example 1

Clinical Trial of the 2S, 4R Ketoconazole Enantiomer Substantially Free of the 2R4S Enantiomer of Ketoconazole in Type 2 Diabetes A Phase 2a trial in patients with type 2 diabetes mellitus was conducted to investigate the safety and tolerability of DIO-902. The trial was the first human clinical study of the 2S,4R enantiomer of ketoconazole administered substantially free of the 2R,4S enantiomer.

The primary objective was to evaluate the safety and tolerability of 14 daily doses of the 2S,4R enantiomer in subjects with type 2 diabetes.

The secondary objective was to determine the pharmacokinetic (PK) profile in plasma of the 2S,4R enantiomer after a single dosing and after fourteen daily doses. In addition the pharmacodynamic activity of fourteen daily doses of the 2S,4R enantiomer, as reflected by changes in blood pressure, total and LDL cholesterol, CRP, plasma and salivary cortisol, cortisol binding globulin, measures of glycemic control (fructosamine, HbA1c and fasting blood glucose levels).

Five (5) dose groups were studied. The dose groups are as follows (N=subjects who completed the study):
1) Ketoconazole ("KTZ") 400 mg po QD (N=8)
2) 2S,4R enantiomer 200 mg po QD (N=10)
3) 2S,4R enantiomer 400 mg po QD (N=−6)
4) 2S,4R enantiomer 600 mg po QD (N=3)
5) Placebo po QD (N=6)
The baseline demographics of the subjects were
Mean age: 55.3
Gender: 59.5% female/40.5% male
Mean BMI: 33.1
Mean duration of Diabetes Mellitus: 4.9 years
Mean HbA1c: 8.1%

The first dose of the study drug was given on Day 1 at 2200 h. Activity markers measured on Day 1 prior to administration of the drug ("Visit 1"). The last dose of study drug was given on Day 14 at 2200 h and activity markers measured on Day 15 ("Visit 3"). Measurements of safety markers were taken on Visits 1 and 3, as well as Visit 2 (Day 8) and Visit 4 (Day 28).

Measures of activity were: A) glycemic control; b) changes in lipid levels (total and LDL-cholesterol); 3) blood pressure and D) CRP as a marker of inflammation.

Glycemic Control

Figure 3:
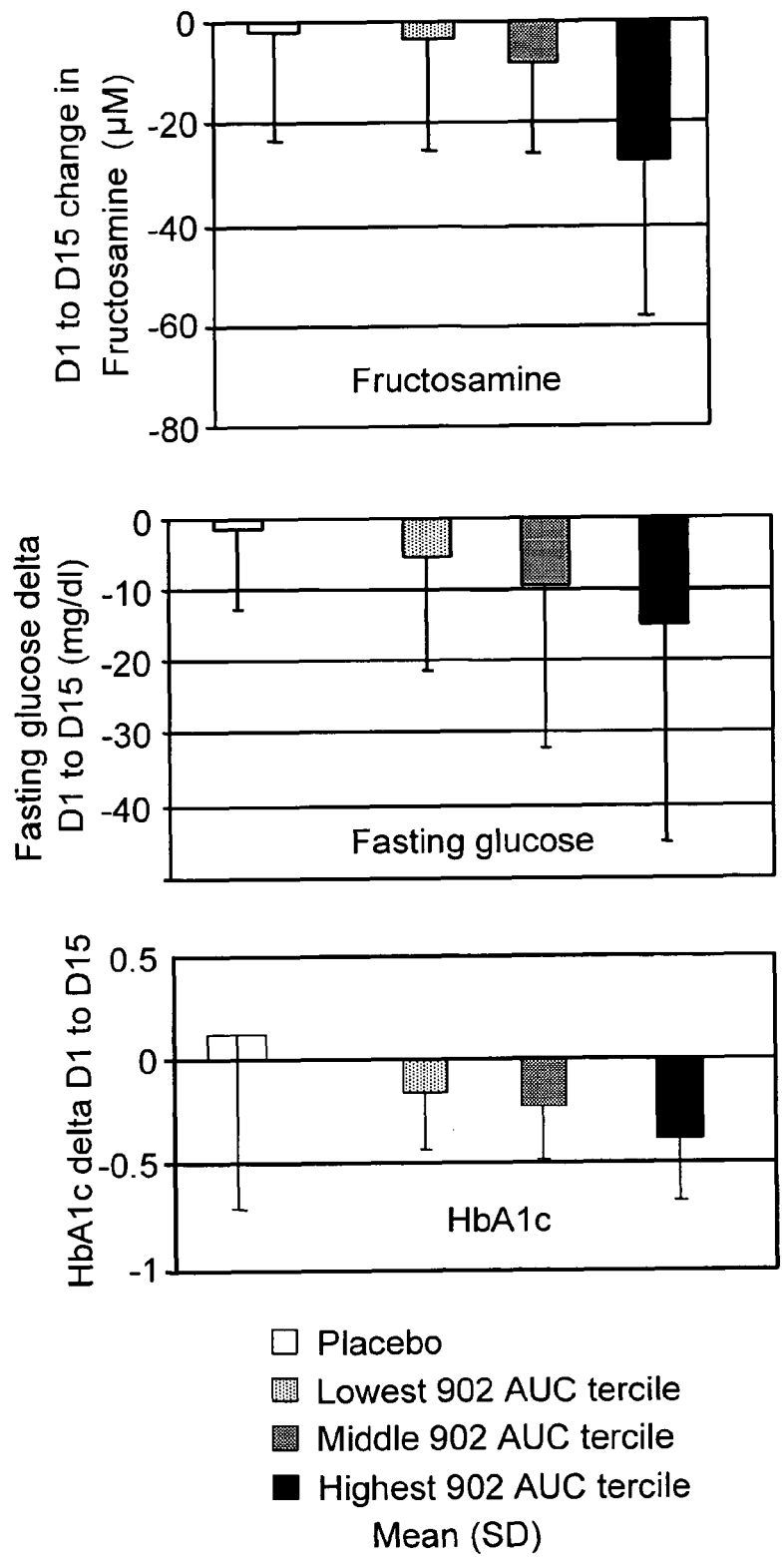
FIG. 3 shows trends to improved glucose homeostasis in subjects receiving a two-week course of DIO-902.

Results of the hemoglobin A1c test (HbA1c) are shown in Table 3 and FIG. 3. This test measure levels of glycated hemoglobin and reflects the average blood glucose level for a subject over the preceding 3 months (approximately). Elevated levels are common in diabetics. Lowering the hemoglobin A1c number can delay or prevent the development of serious eye, kidney, and nerve disease in individuals with diabetes.

TABLE 3

| | HbA1c | | | | |
|---|---|---|---|---|---|
| | | KTZ | DIO-902 | | |
| | Placebo (N = 6) | 400 mg (N = 8) | 200 mg (N = 10) | 400 mg (N = 6) | 600 mg (N = 3) |
| Visit 1 HbA1c (%) mean (SD) | 6.87 (0.664) | 8.05 (1.61) | 8.18 (1.03) | 7.88 (1.35) | 9.10 (1.64) |

TABLE 3-continued

| | HbA1c | | | | |
|---|---|---|---|---|---|
| | | KTZ | DIO-902 | | |
| | Placebo (N = 6) | 400 mg (N = 8) | 200 mg (N = 10) | 400 mg (N = 6) | 600 mg (N = 3) |
| Visit 3 HbA1c (%) mean (SD) | 6.92 (0.897)* | 7.68 (1.47) | 7.86 (1.05) | 7.70 (1.42) | 8.63 (1.45) |
| HbA1c Change vs Baseline (%) mean (SD) | 0.12 (0.388)* | −0.37 (0.27) | −0.32 (0.32) | −0.18 (0.28) | −0.47 (0.35) |

*HbA1c in Subject 04-014 increased from 6.7 to 8.5; if this subject is omitted from the analysis, the mean change in HbA1c is −0.2.

As shown in Table 2, administration of DIO-902 for 14 days produces trends toward a reduction in HbA1c. It is anticipated that administration of drug for a longer period of time, such as twelve weeks or twenty-six weeks, will result in reductions of up to 0.8% or more relative to baseline (e.g., at least 0.4%, at least 0.6% or at least 0.8%).

Figure 2:
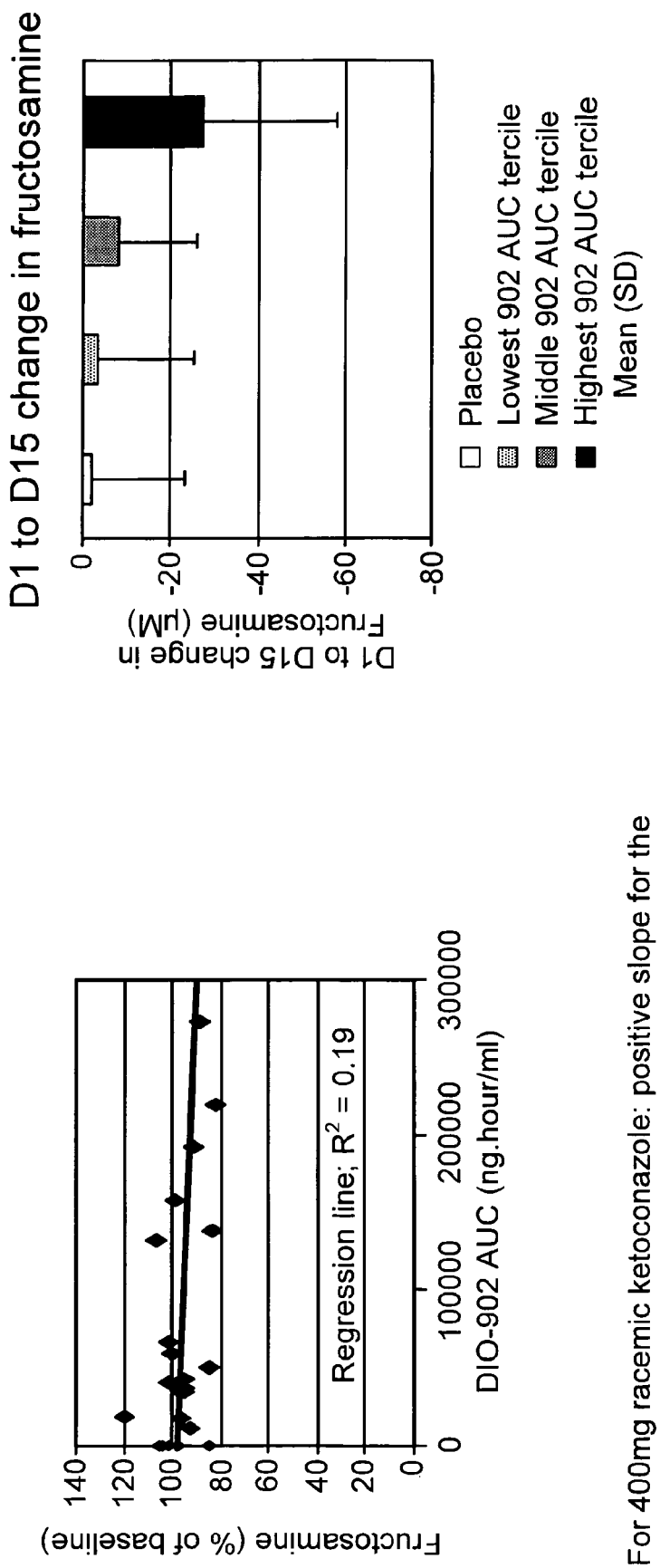
FIG. 2 shows the effect of a two-week administration of a ketoconazole enantiomer (DIO-902) on fructosamine levels based on drug exposure (AUC tercile).

Fructosamine levels were measured at baseline and after two weeks of therapy (see Table 4 and FIGS. 1 and 2). FIG. 1 shows changes in fructosamine levels for each study group on Day 15 compared to baseline. FIG. 2 shows changes in fructosamine levels for each AUC tercile on Day 15 compared to baseline. Fructosamine levels reflect blood glucose levels over the preceding 2-3 weeks. Reductions in fructosamine were greatest in the DIO-902 treatment groups.

TABLE 4

| | Fructosamine | | | | |
|---|---|---|---|---|---|
| | | | DIO-902 | | |
| | Placebo (N = 6) | KTZ 400 mg (N = 8) | 200 mg (N = 10) | 400 mg (N = 6) | 600 mg (N = 3) |
| Visit 1 μmol/L mean (SD) | 236.2 (31.44) | 272.57 (58.92) | 262 (44.67) | 271.00 (27.03) | 276.33 (63.76) |
| Visit 3 μmol/L mean (SD) | 233.8 (30.58) | 270.29 (47.55) | 249.80 (36.19) | 262.67 (25.87) | 247.00 (34.04) |
| Change vs Baseline μmol/L mean (SD) | −2.3 (20.99) | −2.29 (30.37) | −12.20 (26.75) | −8.33 (17.75) | −29.33 (29.74) |

As with HbA1c levels, administration of DIO-902 for 14 days trends toward a reduction in fructosamine. Notably, other glucose-lowering compounds, such as glitazones, may take several weeks for onset of action. It is anticipated that administration of drug for a longer period of time, such as twelve weeks or twenty-six weeks, will result in reductions of up to 40 μmol/L or more relative to baseline (e.g., at least 10 μmol/L, at least 20 μmol/L, at least 30 μmol/L, or at least 40 μmol/L).

Reductions in fasting glucose levels of up to 15 mg/dL were observed in subjects receiving DIO-902 for two weeks (see FIG. 3). It is anticipated that administration of drug for a longer period of time, such as twelve weeks or twenty-six weeks, will result in reductions of up to 25-30 mg/dL or more relative to baseline (e.g., reductions of at least 20 mg/dL, at least 25 mg/dL or at least 30 mg/dL).

Cholesterol Levels

Figure 4:
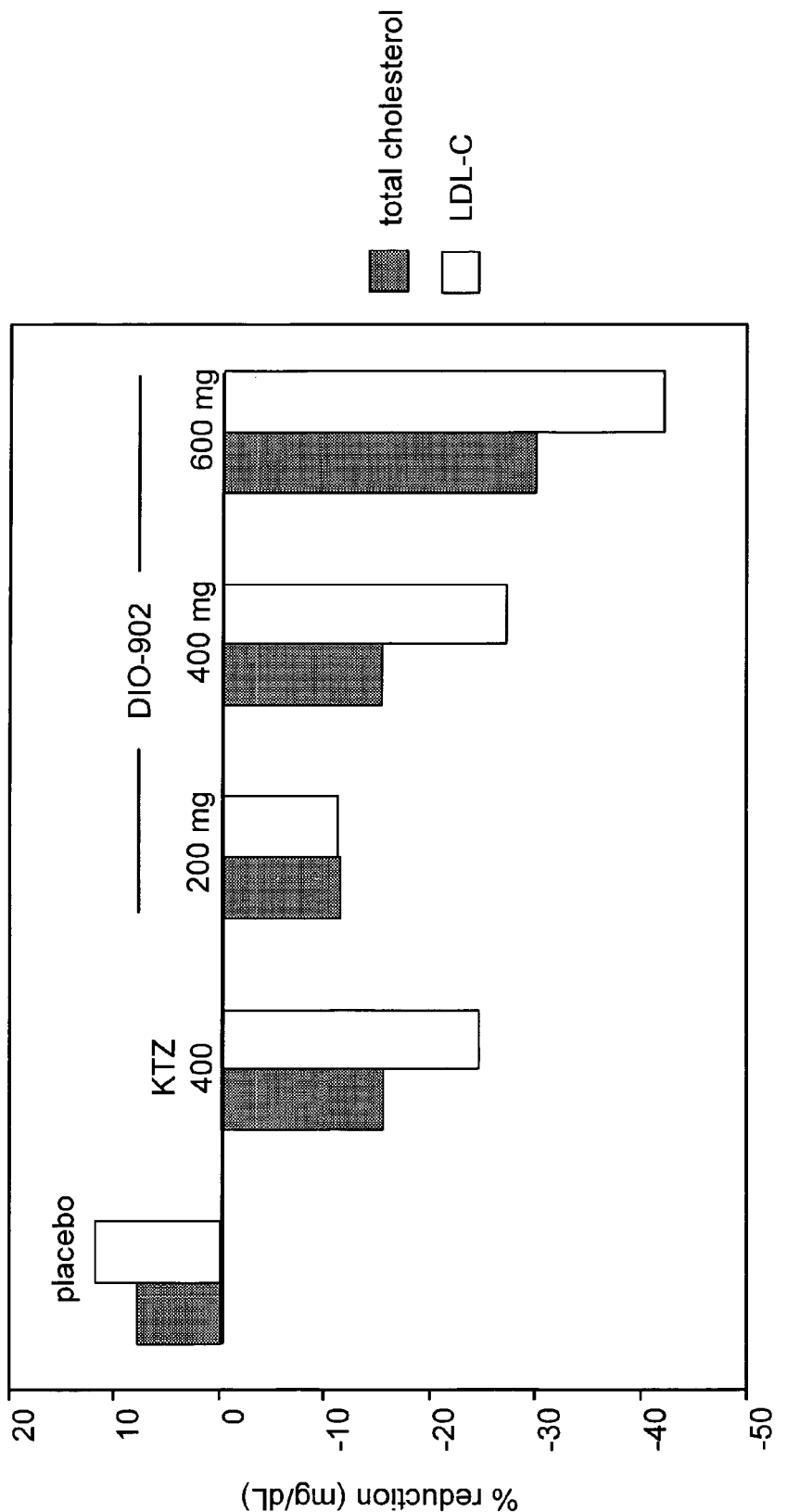
FIG. 4 shows the effect of a two-week administration of a ketoconazole enantiomer (DIO-902) on total cholesterol and LDL-cholesterol levels, presented as % change compared to baseline.
Figure 5:
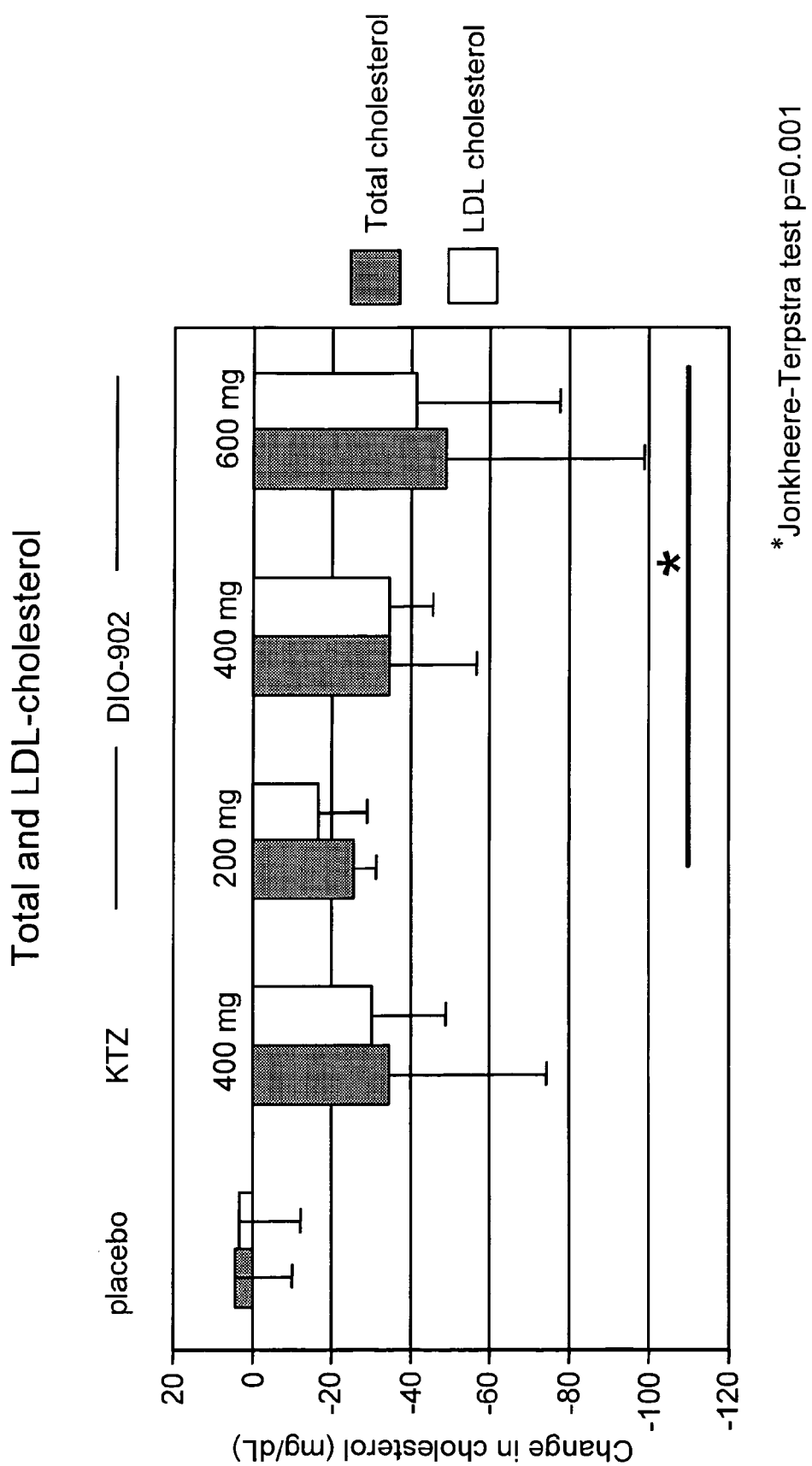
FIG. 5 shows the effect of a two-week administration of a ketoconazole enantiomer (DIO-902) on total cholesterol and LDL-cholesterol levels (presented as change in mg cholesterol per deciliter plasma).

Tables 5 and 6, below, and FIGS. 4 and 5 show changes in total- and LDL-cholesterol levels in the study groups. Statistically significant, dose dependent decreases in total and LDL-C were observed in subjects receiving DIO-902.

TABLE 5

| | Total cholesterol | | | | |
|---|---|---|---|---|---|
| | | | DIO-902 | | |
| | Placebo (N = 6) | KTZ 400 mg (N = 8) | 200 mg (N = 10) | 400 mg (N = 6) | 600 mg (N = 3) |
| Visit 1 mg/dL mean (SD) | 193.2 (27.68) | 198.14 (56.05) | 227.20 (46.44) | 224.50 (21.98) | 195.33 (78.00) |
| Visit 3 mg/dL mean (SD) | 197.7 (23.52) | 164.57 (46.54) | 202.45 (44.17) | 190.50 (33.00) | 130.33 (31.53) |
| Change mg/dL mean (SD) | 4.5 (14.74) | −33.57 (40.17) | −26.10 (5.48) | −34.00 (22.74) | −48.75 (49.98) |
| Mean % change | 7.87 | −15.46 | −11.66 | −15.35 | −29.97 |

TABLE 6

| | LDL cholesterol | | | | |
|---|---|---|---|---|---|
| | | | DIO-902 | | |
| | Placebo (N = 6) | KTZ 400 mg (N = 8) | 200 mg (N = 10) | 400 mg (N = 6) | 600 mg (N = 3) |
| Visit 1 mg/dL mean (SD) | 119.5 (32.43) | 118.71 (50.53) | 141.60 (38.72) | 133.33 (14.99) | 125.67 (58.11) |
| Visit 3 mg/dL mean (SD) | 122.8 (24.98) | 88.29 (37.08) | 124.40 (31.95) | 97.83 (25.10) | 70.67 (29.74) |
| change mg/dL mean (SD) | 14.91 (14.74) | −30.43 (19.35) | −17.20 (11.90) | −35.50 (14.71) | −41.25 (36.32) |
| Mean % change | 11.78 | −24.73 | −11.39 | −27.44 | −42.14 |

It is anticipated that administration of drug for a longer period of time, such as twelve weeks or twenty-six weeks, will result in reductions of total cholesterol of at least 25% to at least 40%, and reductions in LDL-cholesterol of at least 15% or at least 30%.

Blood Pressure

Continuous blood pressure monitoring was performed during Visits 1 and 3. Racemic ketoconazole has been reported to reduce blood pressure. However, no reductions in blood pressure readings were seen either the racemic ketoconazole of DIO-902 groups. Longer dosing regimens may result in beneficial reduction in blood pressure in patients treated with DIO-902.

Markers of Inflammation

Figure 6:
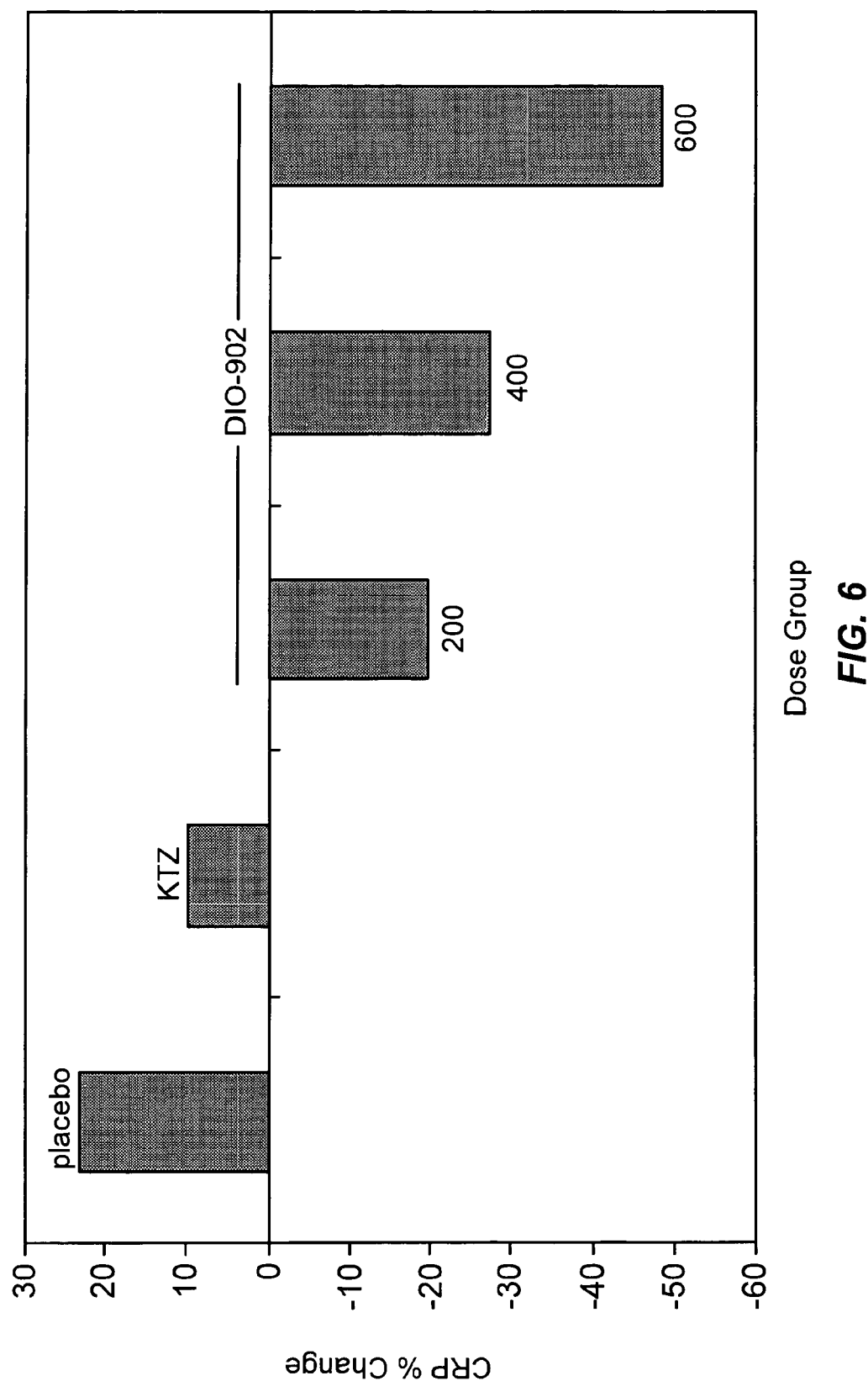
FIG. 6 shows the effect of a two-week administration of a ketoconazole enantiomer (DIO-902) on levels of CRP.

C-Reactive protein (CRP) levels were measured and are shown in Table 7 and FIG. 6. A dose-dependent decrease in CRP was seen in the DIO-902 treatment groups. Significantly, racemic ketoconazole did not reduce CRP levels and actually led to an increase in CRP.

TABLE 7

| | Markers of inflammation C-Reactive Protein (CRP) | | | | |
|---|---|---|---|---|---|
| | Placebo (N = 6) | KTZ 400 mg (N = 8) | 200 mg (N = 10) | 400 mg (N = 6) | 600 mg (N = 3) |
| Visit 1 mg/L mean (SD) | 2.7 (1.36) | 2.28 (1.51) | 6.91 (4.99) | 4.02 (1.37) | 8.35 (6.40) |
| Visit 3 mg/L mean (SD) | 3.2 (1.54) | 2.22 (1.48) | 4.78 (2.87) | 2.95 (1.79) | 5.05 (5.23) |
| Mean % change vs baseline | 23.2 | 9.78 | −19.8 | −27.35 | −48.64 |

Levels of 1-3 mg/L are considered moderate risk; levels of >3 mg/L are high risk.

Reducing CRP levels in diabetic patients is correlated with improved prognosis, or lower risk of developing, microvascular and macrovascular disease. It is anticipated that administration of DIO-902 for a longer period of time, such as twelve weeks or twenty-six weeks will result in reductions of up to 20-50% more relative to baseline (e.g., reductions of at least 20%, at least 30%, at least 40% or at least 50% or more).

Example 2

Absence of Hepatotoxity and Hepatoprotection with DIO-902

Liver toxicity has been observed in some patients receiving racemic ketoconazole. In contrast, evidence of hepatotoxicity was not observed in subjects receiving DIO-902. Moreover, evidence consistent with hepato-protection with DIO-902 was observed. Two (2) patients with liver function test values outside the normal range when measured at baseline normalized with DIO-902 treatment (see Table 8).

TABLE 8

Hepatoprotection with DIO-902 (Sample of LFT results)

| Subject | Dose group | Screening Visit (AST/ALT/AP) | Visit 1 (pre-1st dose) (AST/ALT/AP) | Visit 2 (AST/ALT/AP) | Visit 3 (last dose) (AST/ALT/AP) |
| --- | --- | --- | --- | --- | --- |
| 02-002 | 200 mg DIO-902 | 58/30/110 | 34/22/100 | 30/21/103 | 35/19/97 |
| 04-004* | 400 mg DIO-902 | 48/25/132 | 49/25/108 | 49/28/125 | 46/25/130 |
| 04-010* | 400 mg DIO-902 | 49/27/73 | 48/24/60 | 40/14/82 | 38/19/64 |
| 04-016 | KTZ 400 mg | 33/28/110 | 53/37/109 | 36/19/137 | 31/18/103 |
| 04-014 | PLA | 50/33/126 | 54/39/130 | 59/35/116 | 49/29/109 |

Reference ranges (u/L): AST 0-47; ALT 0-37; AP 40-135

Example 3

Atorvastatin Drug Interaction Study

Figure 7:
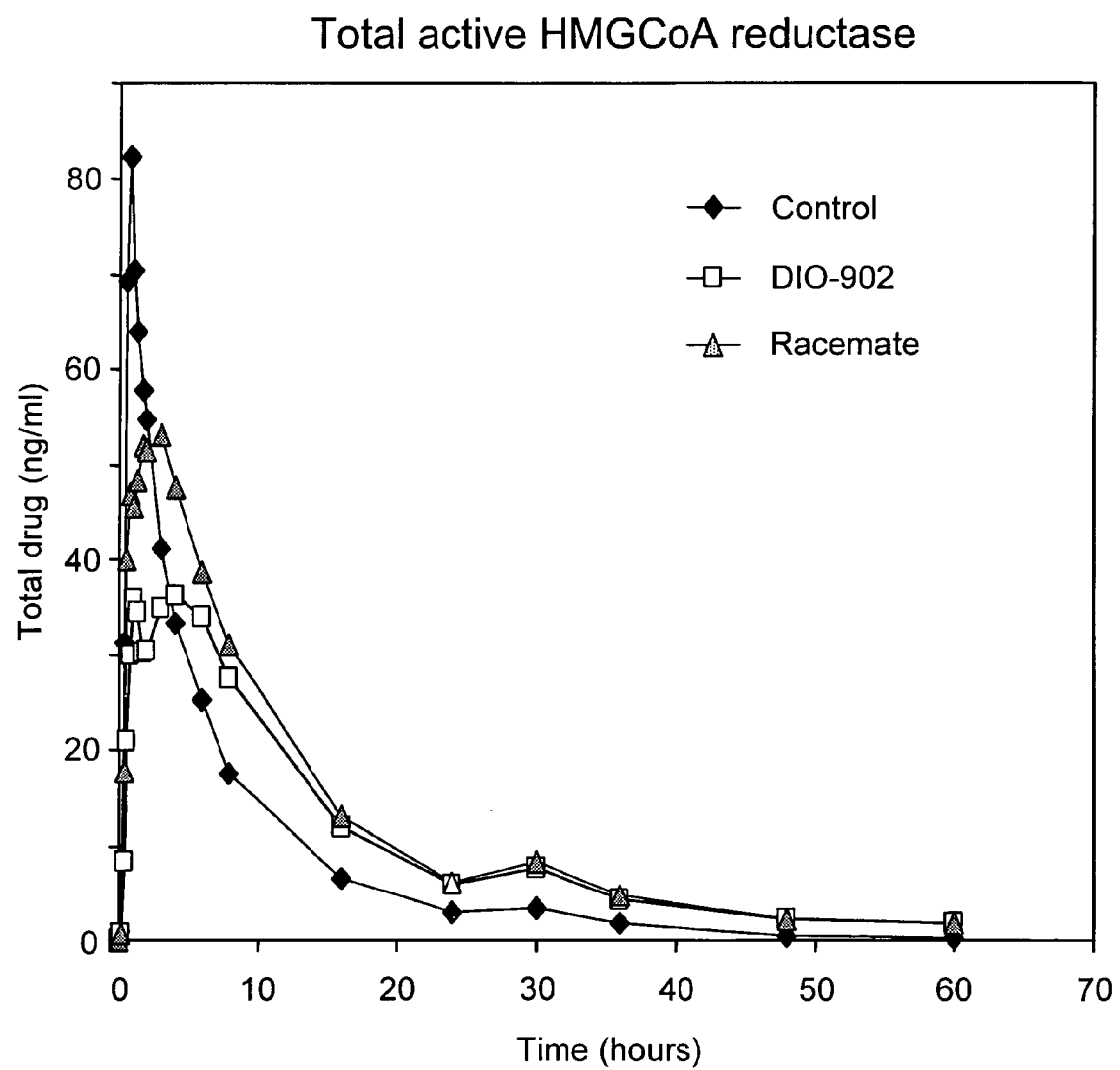
FIG. 7 shows the effect of DIO-902 on atorvastatin pharmacokinetics levels in subjects receiving both drugs.

A 3-way cross-over study (80 mg atorvastatin+400 mg DIO-902, 400 mg racemic ketoconazole, or placebo) was carried out with a washout period of 14 days. As shown in FIG. 7, when plasma levels of total active HMG CoA reductase inhibitor were measured, administration of DIO-902 reduced the Cmax of the total active inhibitor while increasing the AUC relative to the atorvastatin-only control. Racemic ketoconazole did not have as large an effect on the Cmax as did DIO-902. Total active inhibitor is the combined amount of atorvastin and the biologically active metabolites 2-hydroxy atorvastatin and 4-hydroxy atorvastatin.

These data suggest that concurrent therapy with DIO-902 and a cholesterol lowering HMGCoA reductase inhibitor (e.g., a statin such as atorvastatin, lovastatin, simvastatin, pravastatin, fluvastatin, rivastatin, itavastatin, rosuvastatin, and other statins) will result in a reduced Cmax for the HMG CoA reductase activity relative to the racemate or atorvastatin-only control. This allows higher doses of the statin to be administered to a patient whilst avoiding side-effects that would be expected if the HMGCoA reductase inhibitor was administered as a monotherapy.

Example 4

Enantiomer Clearance

The pharmacokinetics of each of the ketoconazole enantiomers was studied following intravenous administration of racemic ketoconazole. Racemic ketoconazole was dissolved in ethanol to 60 mg/ml. Each of three Beagle dogs was administered 0.5 ml bolus (30 mg/dog) intravenously.

Blood was collected from each dog prior to dosing ("0 min") and at 2, 5, 10, 15, 30 min, and 1, 2, 4, 6, 8, and 24 hrs post-dosing. At each timepoint, blood (0.3 mL/sample) was collected and placed into labeled Microtainer® tubes with heparin as the anti-coagulant. The heparinized blood was centrifuged, and the supernatant pipetted off into another set of labeled Eppendorf® tubes. The derived plasma samples were analyzed for each of the two ketoconazole enantiomers (2S,4R and 2R,4S) and pharmacokinetic parameters determined for each of the enantiomers. It was found that the 2S,4R ketoconazole enantiomer had a terminal half life of 1.397 hours and the 2R,4S ketoconazole enantiomer had a terminal half life of 0.93 hours. The corresponding clearances for the two enantiomers were 485 ml/hr/kg (2S,4R) and 1442 ml/hr/kg. These data are consistent with the 2R,4S enantiomer being removed from the circulation into the liver significantly faster than the 2S,4R enantiomer leading to a significantly higher Cmax for the 2R,4S enantiomer within the liver. As the isolated 2S,4R enantiomer does not contain the 2R,4S enantiomer whereas the racemate does, the intraliver Cmax attained for the isolated 2S,4R enantiomer will be less than that for the racemate and as a consequence there is reduced risk of liver damage with the 2S,4R enantiomer as compared to racemic ketoconazole.

The invention, having been described in detail and exemplified above, has a wide variety of embodiments; consequently, while certain embodiments of the invention have been described herein in detail, numerous alternative embodiments are contemplated as falling within the scope of the following claims.

All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same.

What is claimed is:

1. A method of reducing C-reactive protein levels in a patient in need of such reduction, comprising administering a daily dose of a ketoconazole composition comprising 200 mg to 600 mg of a 2S,4R ketoconazole enantiomer substantially free of the 2R,4S ketoconazole enantiomer to said patient.

2. The method of claim 1, further comprising identifying or diagnosing the patient as having elevated plasma C-reactive protein and in need of reduction of systemic inflammation.

3. The method of claim 2, wherein the patient has a plasma C-reactive protein level greater than 3.0 mg/L.

4. The method of claim 2, wherein the patient has a plasma C-reactive protein level greater than 5.0 mg/L.

5. The method of claim 1, wherein the patient is diabetic.

6. The method of claim 1, wherein the patient is diagnosed with metabolic syndrome.

7. The method of claim 1, wherein the daily dose of the ketoconazole composition is 200 mg to 400 mg of the 2S,4R ketoconazole enantiomer.

8. The method of claim 1, wherein the ketoconazole content of the composition is more than 98% of the 2S,4R ketoconazole enantiomer.

9. The method of claim 1, wherein the patient has elevated C-reactive protein levels in plasma.

10. A method of reducing systemic inflammation in a patient in need thereof comprising administering a daily dose of a ketoconazole composition comprising 200 mg to 600 mg of 2S,4R ketoconazole enantiomer substantially free of the 2R,4S ketoconazole enantiomer to said patient.

11. The method of claim 10, wherein the daily dose of the ketoconazole composition is 200 mg to 400 mg of the 2S,4R ketoconazole enantiomer.

12. The method of claim 10, wherein the ketoconazole content of the composition is more than 98% of the 2S,4R ketoconazole enantiomer.

13. The method of claim 10, wherein the patient has elevated C-reactive protein levels in plasma.

14. The method of claim 10, further comprising identifying or diagnosing the patient as having elevated plasma C-reactive protein and in need of reduction of systemic inflammation.

15. The method of claim 10, wherein the patient has a plasma C-reactive protein level greater than 3.0 mg/L.

16. The method of claim 10, wherein the patient has a plasma C-reactive protein level greater than 5.0 mg/L.

17. The method of claim 10, wherein the patient is diabetic.

18. The method of claim 10, wherein the patient is diagnosed with metabolic syndrome.

* * * * *